(12) United States Patent
Schnitzler et al.

(10) Patent No.: US 12,702,392 B2
(45) Date of Patent: Aug. 11, 2026

(54) RETRIEVE DEVICE AND METHOD FOR RETRIEVING OF TISSUE

(71) Applicant: Erbe Elektromedizin GmbH, Tuebingen (DE)

(72) Inventors: Uwe Schnitzler, Tuebingen (DE); Markus Enderle, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 270 days.

(21) Appl. No.: 17/672,362

(22) Filed: Feb. 15, 2022

(65) Prior Publication Data

US 2022/0273278 A1 Sep. 1, 2022

(30) Foreign Application Priority Data

Feb. 26, 2021 (EP) .................................... 21159686

(51) Int. Cl.
*A61B 17/00* (2006.01)
*A61B 1/018* (2006.01)
*A61B 1/307* (2006.01)

(52) U.S. Cl.
CPC ........ *A61B 17/00234* (2013.01); *A61B 1/018* (2013.01); *A61B 1/307* (2013.01); *A61B 2017/00287* (2013.01); *A61B 2017/00942* (2013.01)

(58) Field of Classification Search
CPC ... A61B 17/00234; A61B 1/018; A61B 1/307; A61B 2017/00287; A61B 2017/00942; A61B 10/02; A61B 50/30; A61B 2050/314
See application file for complete search history.

(56) References Cited

U.S. PATENT DOCUMENTS 5,190,542 A 3/1993 Nakao et al.
5,341,815 A 8/1994 Cofone et al.
5,643,283 A * 7/1997 Younker .......... A61B 17/00234 606/17
5,836,953 A * 11/1998 Yoon ................. A61B 17/3462 606/127
6,228,095 B1 5/2001 Dennis
(Continued)

FOREIGN PATENT DOCUMENTS

CN 204816230 U 12/2015
CN 105381649 A 3/2016
(Continued)

OTHER PUBLICATIONS

Polycarbonate (PCTE) membrane filters, 0.1 micron, 25mm, 100/PK. Sterlitech Corporation. (Feb. 19, 2017). https://www.sterlitech.com/hydrophilic-polycarbonate-membrane-filter-pct0125100.html (Year: 2019).*

*Primary Examiner* — Andrew P. Restaino
(74) *Attorney, Agent, or Firm* — Blank Rome LLP

(57) ABSTRACT

A retrieve device for retrieving tissue having a retrieve bag that is at least in part a hydrophilic water permeable filter diaphragm. The filter diaphragm may have a pore width that allows for blocking passage of pathogen cells or other pathogen material. The pores width may also be large enough to allow water to exit out of the retrieve bag. Liquid in the retrieve bag can be expelled through the filter diaphragm and thus does not contribute the volume of the retrieve bag.

15 Claims, 5 Drawing Sheets

(56) References Cited

U.S. PATENT DOCUMENTS

| | | | | |
|---|---|---|---|---|
| 6,350,267 | B1 | 2/2002 | Stefanchik | |
| 7,743,474 | B2 * | 6/2010 | May | B65D 33/2508 24/585.12 |
| 2001/0002437 | A1 | 5/2001 | Pagedas | |
| 2007/0098304 | A1 | 5/2007 | May | |
| 2011/0137334 | A1 * | 6/2011 | Anderson | A61B 17/221 606/200 |
| 2012/0158010 | A1 | 6/2012 | Menn et al. | |
| 2013/0023895 | A1 | 1/2013 | Saleh | |
| 2013/0317515 | A1 * | 11/2013 | Kuroda | A61B 17/3478 606/113 |
| 2017/0325930 | A1 * | 11/2017 | Montgomery | A61B 17/1215 |
| 2019/0059948 | A1 | 2/2019 | Kim et al. | |
| 2020/0060665 | A1 | 2/2020 | Jensen | |

FOREIGN PATENT DOCUMENTS

| | | | |
|---|---|---|---|
| CN | 205948691 | U | 2/2017 |
| DE | 699 07 796 | T2 | 4/2004 |
| EP | 2 353 511 | A1 | 8/2011 |
| EP | 2 497 429 | A1 | 9/2012 |
| EP | 2 605 709 | A2 | 6/2013 |
| WO | WO 93/15671 | A1 | 8/1993 |
| WO | WO 2011/049918 | A1 | 4/2011 |
| WO | WO 2012/026809 | A2 | 3/2012 |

* cited by examiner

RETRIEVE DEVICE AND METHOD FOR RETRIEVING OF TISSUE

CROSS-REFERENCE TO RELATED APPLICATION

This application claims priority to European Application No. 21159686.1, filed Feb. 26, 2021, the entirety of which is incorporated by reference herein.

TECHNICAL FIELD

Embodiments of the invention refer to a retrieve device for retrieving tissue from a human or animal patient, particularly from body cavities filled with liquid, such as the urinary bladder, for example.

BACKGROUND

Devices and arrangements for retrieving tissues that have been released during a surgical intervention on a patient from contagious tissue are known, e.g. from DE 699 07 796 T2. The instrument comprises an insertion tube through which an axially movable plunger tube extends. The latter is connected with arcuate-shaped holding rails at its distal end on which a bag hangs. A thread guided through the upper edge of the bag allows closing thereof.

Further retrieve devices with bags are known from WO 93/15671, U.S. Pat. No. 6,350,267 B1, EP 2 353 511 A1, US 2012/0158010 A1, U.S. Pat. No. 6,228,095 B1, U.S. Pat. No. 5,341,815, EP 2 605 709 A2 and WO 2012/026809 A2 as well as from EP 2 497 429 A1. The last-mentioned document discloses a retrieve bag that is provided with a gas outlet. As such a hydrophobic air filtering material or such a diaphragm is provided. The hydrophobic filtering material avoids passage of liquid due to its water-repelling effect, but allows gas to exit.

SUMMARY

During tissue resection in liquid-filled body cavities, e.g. the urinary bladder, it can be essential to completely take up pathologically changed tissue, e.g. pathologically changed tissue, as far as possible as large non-separated piece and to remove it from the body cavity without leaving individual tissue scraps or cells behind. Possible retrieve bags have to be dimensioned spaciously accordingly. On the other hand, such retrieve bags have to be removed out of the patient through access paths, e.g. the working channel of an endoscope.

Starting therefrom it is the object of embodiments of the invention to provide a retrieve device and a method for retrieving tissue with which tissue can be reliably taken up and by means of which the tissue can be reliably removed out of the patient body via the working channel of an access instrument, such as an endoscope out of the patient body.

This object is solved, for example, by means of the features of claim 1 or 15:

The retrieve device according to embodiments of the invention comprises a retrieve bag for retrieving cells out of a body internal liquid filled cavity of a patient. The liquid can be an endogenous liquid, e.g. urine, bile, pancreatic secretion, liquor or also an externally supplied liquid, such as sodium chloride solution. The retrieve bag comprises a filling opening and a bending resistant or flexible traction means that is connected with the retrieve bag. In addition the retrieve bag comprises a section made of hydrophilic water permeable filter diaphragm. Such a filter diaphragm means any filter diaphragm, the pore width thereof is so small that tissue scraps or cells of the retrieved tissue are reliably retained. Thereby it is possible to reduce the volume of the retrieve bag when it is closed, by pressing out water to a volume that is not remarkably larger than the volume of the retrieved tissue. The retrieve device is thus particularly suitable for use in liquid-filled body cavities. It is avoided that the retrieve bag has unnecessary large required space, due to a quantum of taken up water. In this manner it can be achieved to also locate relatively large tissue sections as a whole in the retrieve bag and—after urging out excessive liquid—yet to remove the retrieve bag through the relatively narrow working channel of an access-allowing instrument, e.g. an endoscope or cystoscope out of the patient.

Particularly during use of a cystoscope that typically comprises only one working channel, the retrieve device according to embodiments of the invention is of major advantage. Due to the possibility to remove excessive liquid out of the retrieve bag and thus to reduce its volume, the retrieve bag can hold large tissue pieces, such that tumors can be removed as a whole without having to separate them. This also relieves the surgeon from the necessity of changing between instrument and retrieve device multiple times.

The filling opening of the retrieve bag can be provided with a closing device that can be realized, for example, by a profile strip closure. With it a fluid-tight closure of the retrieve bag is possible. The profile strip closure comprises two complementary strips that can be latched with each other along their entire length and thereby provide a fluid-tight closure of the filling opening of the retrieve bag. For this purpose the two strips of the profile strip closure can be sealingly and non-releasably connected on the proximal end and the distal end in order to let no liquid leak in the closed condition that could contain any cells.

The closure device comprises an open position in which the retrieve bag is wide open and can take up tissue as well as liquids. Moreover, the closure device comprises a closed position in that the receive opening of the retrieve bag is closed. Preferably the closure device is biased toward its open position. The two strips of the profile strip closure are domed away from each other resiliently.

The retrieve bag can comprise two preferably flexible sidewalls that abut against each other, if the retrieve bag is closed. This helps during urging out liquid, particularly water, from the retrieve bag. The flexibility of the sidewalls is preferably so high that the retrieve bag can be convoluted to a winding that fits through the working channel of an endoscope or cystoscope.

A wring out device can be assigned to the retrieve bag. It can be used to urge liquid, particularly water, that has been taken up by the retrieve bag out of the retrieve bag after it has been closed. The hydrophilic filter diaphragm allows water and aqueous solutions to exit, however, retains cells and tissue parts.

The retrieve bag can be manufactured entirely from the hydrophilic water permeable filter material. It can, however, also comprise at least one non-water permeable section, e.g. in form of a plastic foil, from which one or both side walls of the retrieve bag are made. The plastic foil can comprise windows at one or multiple locations in or on which the hydrophilic water permeable filter diaphragm is attached.

The filter material is preferably a fleece, a woven fabric, a braid, a knitted fabric or a porous foil. The filter material can thereby be selected from the group of the following materials:

Polyethersulfone (PES) with or without support material, e.g. polyester, acrylic polymer, polyamide (PA) or polyethylene terephthalate, polysulfone (PS), polyethylene terephthalate hydrophilized polytetrafluorethylene (PTFE), cellulose acetate (CA), cellulose nitrate (CN), cellulose acetate with cellulose nitrate (MCE), nylon (NY), polycarbonate (PCTE), polyvinylidene difluoride (PVDF). In addition, the filter material can consist of coated fibers or micro-perforated foils, e.g. of cellulose fibers, e.g. a paper-like fleece of cellulose fibers that can be coated with an impregnation of for example 2,2-dimethoxy-2-phenylacetophenone as well as 3-(1H,1H,2H,2H-perfluorooctyl)-1-vinylimidazolium iodide and 3,3'-(hexane)-1,6-diyl)bis(1-vinylimidazolium) dibromide as well as acetonitrile, propane-1-ol. The following materials have been turned out to be particularly suitable: polyetheresulfone (PES), acrylic polymer, polyamide (PA) and polyethylene terephthalate.

The filter material preferably comprises a maximum pore size of less than 5 μm. Smaller upper limits for the pore size can be provided, such as 3 μm, 2 μm, 1.2 μm, 0.8 μm, 0.65 μm, 0.45 μm or 0.2 μm. Although basically very small pore sizes can be used, it is also considered not to set the smallest pore size smaller than 0.2 μm, such that a higher water permeability of the filter diaphragm is obtained, concurrently however typical tumor cells are reliably retained.

With the so far described retrieve device an embodiment of an inventive retrieve method can be carried out as follows:

First, the retrieve bag is, for example introduced through the working channel of an endoscope or cystoscope in folded or convoluted condition in a body cavity and is released there, such that it is ready for receiving cell material. After the material to be retrieved has been introduced in the retrieve bag, the retrieve bag is closed. Subsequently, liquid enclosed in the retrieve bag is removed through the filter diaphragm out of the retrieve bag in order to reduce its volume. The retrieve bag having been compacted with regard to its volume in this manner can now be again removed through the working channel of the endoscope or cystoscope or another access out of the body cavity of the patient.

BRIEF DESCRIPTION OF THE DRAWINGS

Details and advantageous embodiments of the invention are apparent from the individual figures of the drawings, the corresponding description as well as the dependent claims. The drawings show:

DETAILED DESCRIPTION

Figure 1:
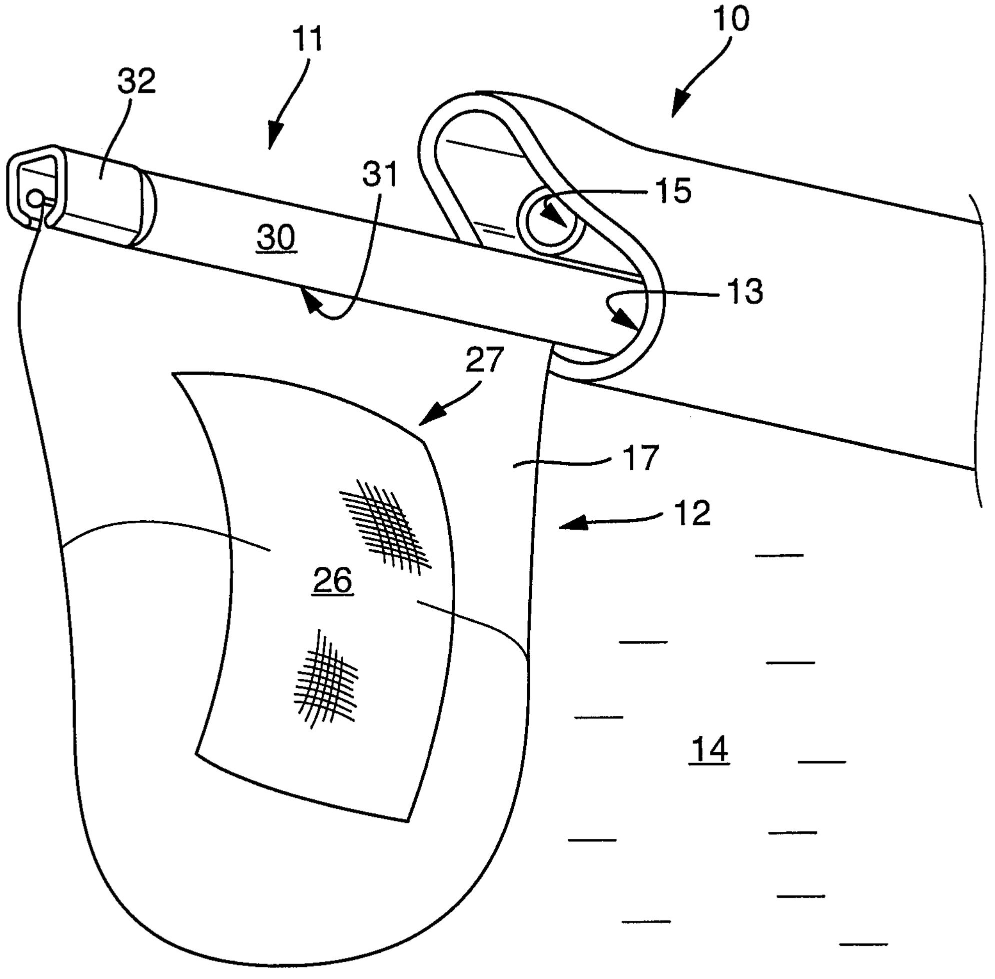
FIG. 1 the distal end of the cystoscope with a retrieve device having a retrieve bag supported in the cystoscope in a perspective illustration, FIG. 2 the retrieve bag of FIG. 1 in open condition ready to receive cell material in perspective illustration, FIG. 3 an illustration in part of the upper edge of the retrieve bag in perspective sectional illustration for illustration of its closure device, FIG. 4 the closure device of FIG. 3 in closed condition in a vertical section, FIG. 5 a portion of the wall of the bag with filter diaphragm, FIG. 6 a modified embodiment of the wall of the retrieve bag with filter diaphragm, and FIG. 7 a retrieve device with wring out device for the retrieve bag.

Inserted into a cystoscope 10 a retrieve device 11 and a retrieve bag 12 being part thereof is illustrated in FIG. 1. The retrieve device 11 is insertable into a body cavity 14 of a patient through a working channel 13 of cystoscope 10, as e.g. into the urinary bladder or another body cavity in which a surgical measure is to be executed such as a tumor resection or another tissue resection. The body cavity 14 is thereby typically filled with liquid, such as an endogenous liquid, e.g. urine, bile, pancreatic secretion, liquor or a supplied liquid, e.g. sodium chloride solution. The cystoscope 10 comprises only one working channel 13 through which the different instruments can be inserted into the body cavity 14. Such instruments are shifted through the working channel 13 alternatingly with retrieve device 11. The cystoscope 10 comprises an optical device 15 by means of which the surgery location can be monitored. The optical device 15 can be a camera with optics and illumination or another image transmitting device.

Instead of the cystoscope 10 also an endoscope can be used that comprises additional working channels, as for example a channel instead of the optical device 15 through which the instruments can be transferred into the body cavity 14, whereby as an option concurrently the retrieve device 11 can be located in the working channel 13.

Such instruments can be, for example electrosurgical instruments with wire electrodes, loop electrodes or the like by means of which tissue portions can be separated from other tissue compound structures. The retrieve bag serves for reception and reliable enclosure of such tissue parts that—being reliably packed in the retrieve bag—can then be removed out of the body cavity 14 through the working channel 13.

Figure 2:
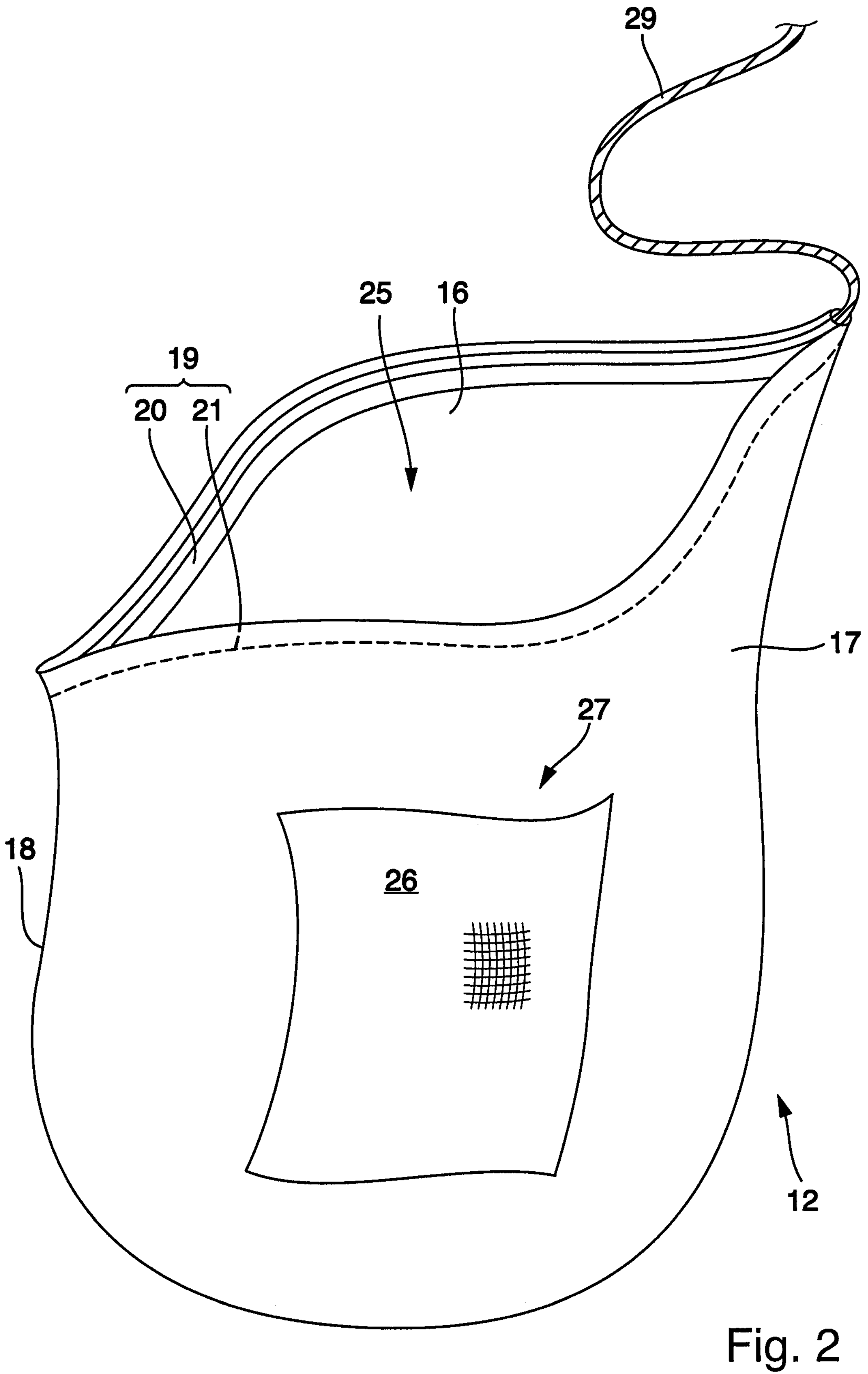

The retrieve bag 12 is separately illustrated in FIG. 2. It preferably comprises two flat sidewalls 16, 17 that can consist, for example, from a thin flexible plastic material, e.g. a plastic foil, that consists of polyethylene or a similar material, for example. The sidewalls 16, 17 are contoured and transition at an edge 18 into one another or are connected with one another there, such that they can be placed flat onto each other.

Figure 3:
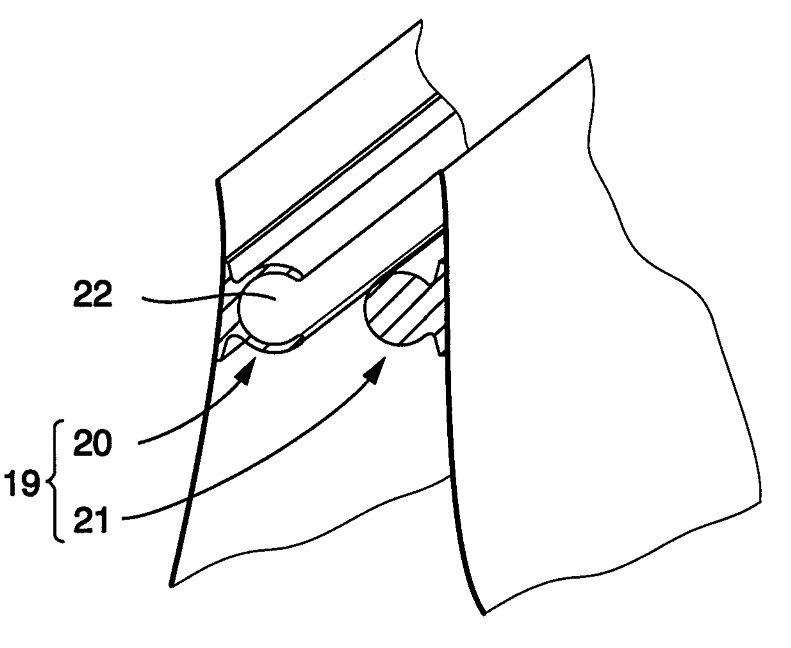
Figure 4:
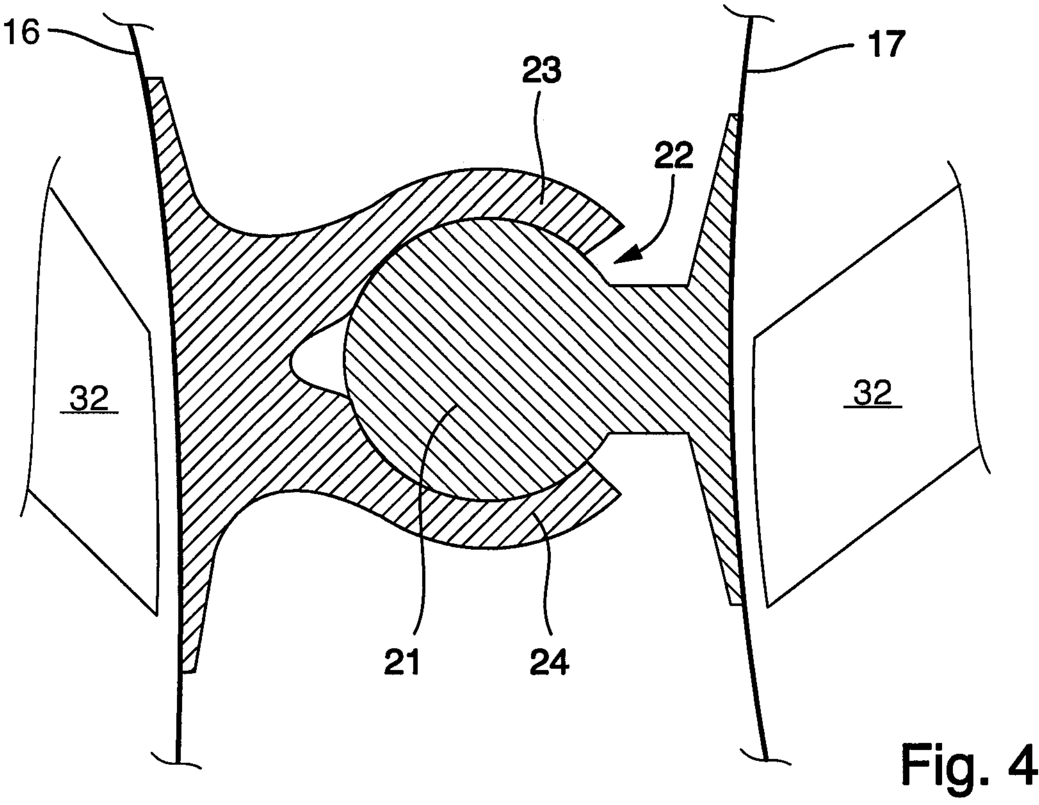

The sidewalls 16, 17 are connected with a closure device 19 on top that is configured as profile strip closure, for example, and comprises two complementary strips 20, 21 for this purpose, for example. The strip 20 is, for example, C-shaped in cross-section, as shown in FIG. 3, and comprises therefore two resilient legs that limit a channel 22 between each other. The strip 21 is preferably formed by a round profile, as shown in FIG. 4, that fits into the channel 22 between the resilient legs 23, 24.

The strips 20, 21 of the closure device 19 are preferably made of a flexible plastic. As shown in FIG. 2, they are slightly domed in relaxed position such that they open a filling opening 25 on the retrieve bag 12. FIG. 2 illustrates the filling opening 25 in open position. If the two strips 20, 21, however, interlock along its respective entire length, the retrieve bag 12 is closed, the closure device 19 is then in closed position. Due to the curvature of strips 20, 21 in relaxed condition, the closure device 19 is, however, biased toward its open position, as apparent from FIG. 2. Is it however closed, a potentially provided stiffness of the sidewalls 16, 17 results in that they tend to abut against each other, whereby the interior enclosed by the retrieve bag 12 has the tendency to shrink.

The retrieve bag 12 can be entirely or, as indicated in FIGS. 1 and 2, also only partly consist of a hydrophilic water permeable filter diaphragm 26 that covers a section 27 of the retrieve bag 12 or its sidewall 17. An identical or similar filter diaphragm 26 can also be provided on the other sidewall 16 if required.

Figure 5:
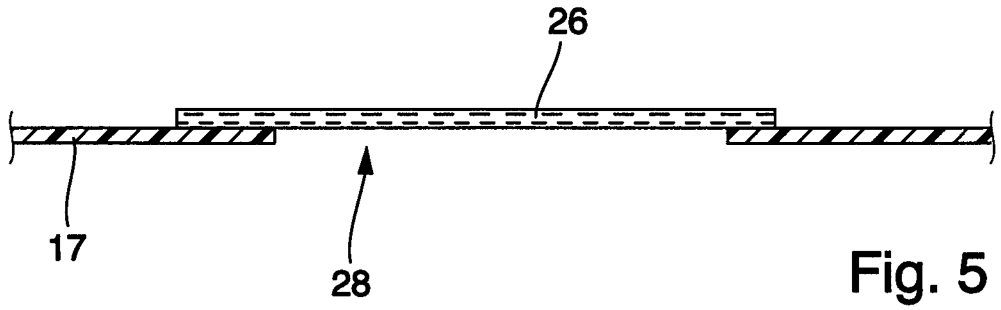

The filter diaphragm 26 is illustrated separately in FIG. 5. It is arranged on a window 28 of the otherwise preferably water impermeable sidewall 16 and tightly connected with the edge of window 28. For example, the filter diaphragm can be arranged on the side of the sidewalls 16 or 17 facing the interior and can be adhesively bonded or welded to the edge of window 28.

Filter diaphragm 26 can be a fleece or porous foil and can contain one or multiple materials selected from the following group or can consist thereof:

Polyethersulfone (PES), acrylic polymer, polyamide (PA) or polyethylene terephthalate, polysulfone (PS), hydrophilized polytetrafluorethylene (PTFE), cellulose acetate (CA), cellulose nitrate (CN), cellulose acetate with cellulose nitrate (MCE), nylon (NY), polycarbonate (PCTE) and/or polyvinylidene difluoride (PVDF).

Alternative filter materials are possible as far as they are made of a hydrophilic material or of a material with hydrophilic coating or equipment. Pores extend through the filter material that extend from one flat side of filter diaphragm to its other flat side and thus form a fluid passage through which water can exit from the interior of retrieve bag 12 into the environment. The upper limit for the size of the pores is preferably below 12 μm and thus below the cell size of tumor cells. Preferably the largest pore diameter is at most 5 μm, further preferably at most 3 μm or less. Preferably the pore size only slightly falls below a value of 0.2 μm. In a particularly preferred embodiment the pore diameter is larger than 0.2 μm.

The retrieve bag 12 is, as apparent from FIG. 2, provided with a traction means 29, e.g. a plastic wire or a cord that is preferably connected with a corner of retrieve bag 12 at which the closure device 19 ends. The traction means 29 comprises a length that is longer than the length of the endoscope or cystoscope 10, such that the end of the traction means 29 of retrieve bag 12 according to FIG. 1 is accessible from outside (outside the patient). The traction means 29 extends through a push rod 30 that can be configured like a tube and that comprises a longitudinal slit 31 at its distal end. The longitudinal slit is dimensioned such that the closure device 19 is closed, i.e. the strips 20, 21 are pressed into one another in a latching manner, if the retrieve bag is pulled into the longitudinal slit 31 by means of a relative movement between push rod 30 and traction means 29. Preferably traction means 29 is flexible and thus can transmit traction forces, but no pushing forces.

The retrieve device described so far operates as follows:

For retrieving tissue the retrieve bag 12 can first be convoluted and can be positioned before or in an end 32 of push rod 30, whereby the traction means 29 extend through push rod 30 or along the latter. By means of push rod 30 the convoluted retrieve bag 12 is now pushed through working channel 13 of endoscope or cystoscope 10 into the body cavity 14 of a patient. The retrieve bag 12 is released upon exiting working channel 13 of endoscope or cystoscope 10 such that a filling opening 25 opens the interior of retrieve bag 12. The strips 20, 21 spring away from one another such that also between the sidewalls 16, 17 a space is spanned. The surgeon can now remove tissue in one piece from a surgery location, e.g. by means of another instrument guided to another working channel 15 and transport it through the filling opening 25 into retrieve bag 12. If this process step is completed, push rod 30 is moved in distal direction, whereby traction means 29 remain axially immovably held, such that bag 12 is unable to follow the axial movement of push rod 30. As a consequence, push rod 30 moves over the upper end of retrieve bag 12 by means of its longitudinal slit 31 and thereby closes the closure device 19 permanently. The closed retrieve bag 12 remains closed and cannot be opened inside body cavity 14, also not unintentionally. The traction means 29 can indeed pull retrieve bag 12 into longitudinal slit 31, but cannot push it out anymore. If the proximal end of traction means 29 is connected with the proximal end of push rod 30, the retrieve bag can also not be pushed out of the longitudinal slit 31, if it is pulled through the working channel 13 out of cystoscope 10 or endoscope by means of push rod 30. For this purpose connection means can be provided at the proximal ends of push rod 30 and the traction means.

Due to the stiffness of the sidewalls 16, 17 and/or also the stiffness of the filter diaphragm 26, the interior of retrieve bag 12 has now the tendency to reduce its volume. Liquid, particularly water or aqueous substances taken up out of the body cavity 14 that are present in the retrieve bag 12, can exit through the hydrophilic filter diaphragm 26 out of retrieve bag 12. The retrieved tissue, however, remains inside retrieve bag 12. The latter can now be shrunk carefully, e.g. convoluted in that it is wound around the end of push rod 30 by means of its rotation and is retracted through the working channel 13. It can also be removed out of the patient together with the endoscope or cystoscope 10.

Figure 6:
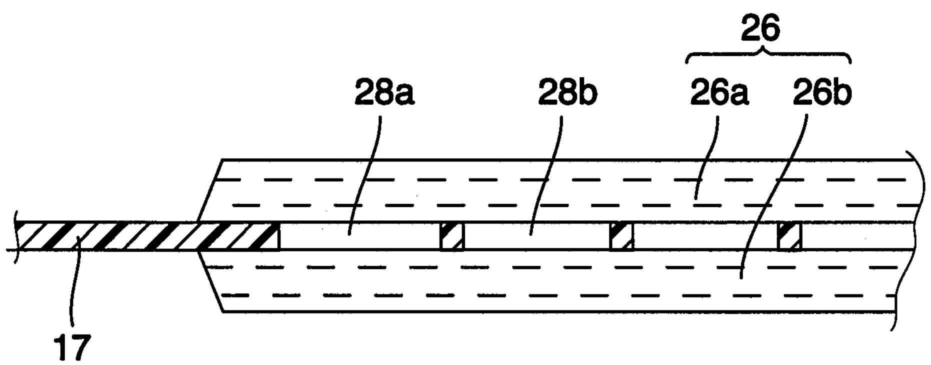

Modifications of the invention are possible. For example, according to FIG. 6, a number of smaller windows **28*a*, 28*b*, etc. can be provided instead of one window 28 in sidewall 17 that are covered by filter diaphragm 26. It is in addition possible to provide multiple filter diaphragms 26*a*, 26*b* instead of one single filter diaphragm 26. The filter diaphragms 26*a*, 26*b* can be considered as layers of a filter diaphragm, whereby the intermediate punched sidewall 17 forms a support. As an alternative, the filter diaphragms 26 according to FIG. 5 or also the filter diaphragms 26*a* and/or 26*b* according to FIG. 6** can have a multi-layer configuration respectively. The individual layers can be configured from identical or also from different materials that can be selected from the material list mentioned above. Other materials having similar functions are possible. They can be directly stacked onto one another or arranged with distance to each other. Particularly, many diaphragms can be provided from individual foils having openings that are larger than the tumor cells, e.g. (also remarkably) larger than 12 μm. By connection of multiple of such foils in a layered manner with different orientations, a compound diaphragm with smaller openings is created, because a superposition of the individual foils results. This simplifies the manufacturing and lowers the resistance of water flowing therethrough.

Figure 7:
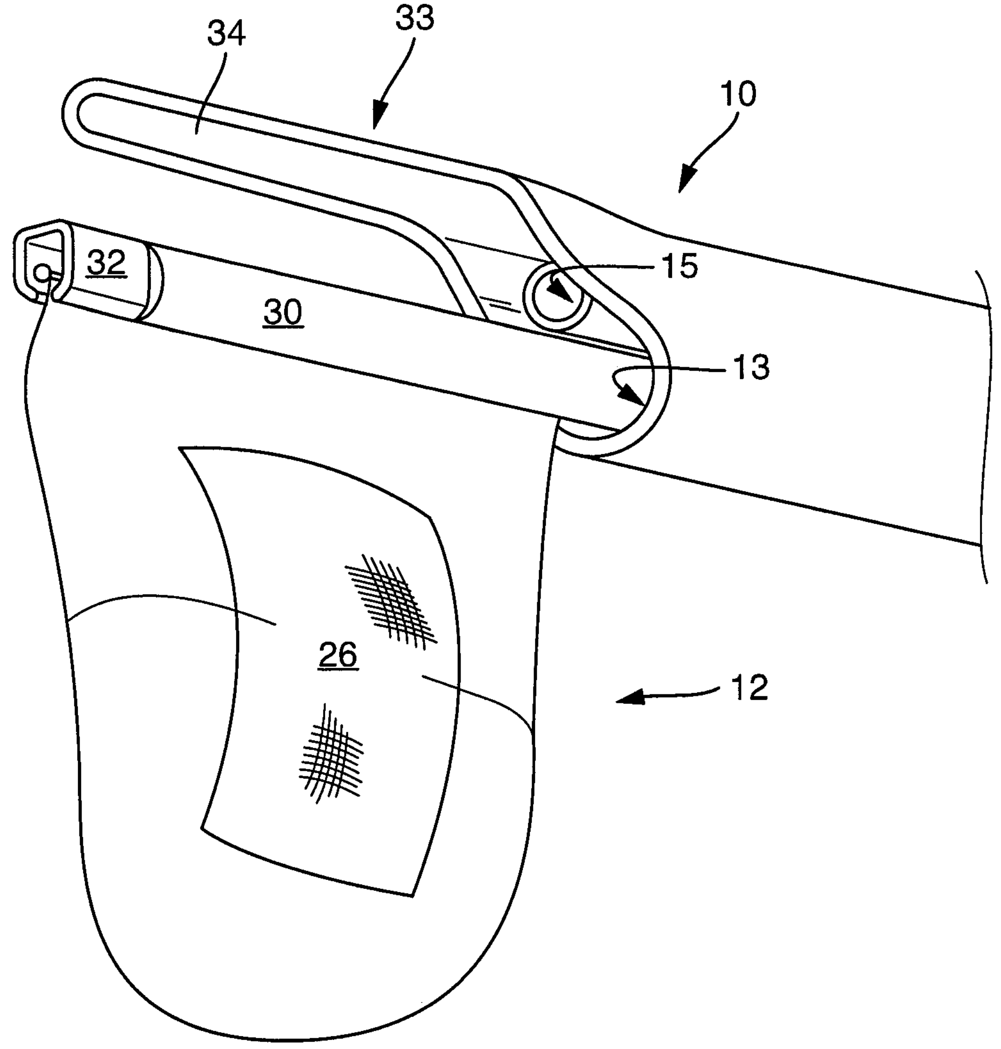

Another embodiment is shown in FIG. 7. A wring out device 33 is assigned to the retrieve bag 12 there. It can be configured, for example, as finger-like rigid or as top part cap configured extension 34 that extends away from the cystoscope 10 or an endoscope in distal direction. In an endoscope a respective rod can be inserted through working channel 15 instead of the extension, the distal end of which forms or replaces extension 34. If push rod 30 is rotated, finger 34 impedes a rotation of retrieve bag 12 and thus presses water out of its interior that can exit through filter diaphragm 26.

According to embodiments of the invention, for retrieving tissue, particularly pathogen tissue out of a body cavity of a patient, a retrieve device having a retrieve bag 12 is provided that consists completely or partly of a hydrophilic water permeable filter diaphragm 26. The filter diaphragm 26 comprises a pore width of preferably less than 12 μm, further preferably less than 8 μm and in the preferred case less than 5 μm in order to reliably avoid passage of pathogen cells or other pathogen material. However, the pores are at least so large that water can easily exit out of the retrieve bag 12. In this manner when filled retrieve bag 12 requires only the volume that is occupied by the contained tissue to be removed. Liquid provided inside retrieve bag 12 can be urged out of retrieve bag through filter diaphragm 26 and thus does not contribute to its volume. This allows taking up relatively large tissue pieces during tumor removal. It is thus possible to remove tumors as a whole without having to separate them inside the body cavity. The danger of spreading malign tissue and the danger of recurrence associated therewith are thus significantly reduced.

The invention claimed is:

1. A device for retrieving tissue, the device comprising:

a retrieve bag comprising:

two separate first and second sidewalls, at least one of the first and second sidewalls having a hydrophilic water permeable filter diaphragm, wherein the hydrophilic water permeable filter diaphragm comprises an arrangement of one or more layers of filter materials, wherein the one or more layers of filter materials is a fleece or porous foil and wherein the one or more layers of filter materials has a pore size of less than 5 μm;

a closure device comprising, a first strip coupled to the first sidewall, the first strip having a portion having a C-shaped cross section, and a second strip coupled to the second sidewall, the second strip having a portion having a rounded cross section, wherein the first and second strips define an opening configured to capture tissue from a patient and the first and second strips are configured to latch together to form a seal when the portion of the second strip having the rounded cross section is inserted into the portion of the first strip having the C-shaped cross section; and a push rod having a longitudinal slit configured to receive the retrieve bag, and wherein a part of the retrieve bag comprising the closure device is configured to be pulled into the longitudinal slit by a wire or cord to close the closure device, the longitudinal slit configured to press the rounded cross section of the second strip into the C-shaped cross section of the first strip with sufficient closing force to latch the first strip and the second strip together as the first and second strips are pulled with relative motion between the push rod and both the first and second strips into the longitudinal slit.

2. The device for retrieving tissue according to claim 1, wherein one end of the wire or cord is connected to the retrieve bag.

3. The device for retrieving tissue according to claim 2, wherein one end of the wire or cord is connected to a corner of the retrieve bag at which the closure device ends.

4. The device for retrieving tissue according to claim 1, wherein the push rod is configured to be rotated in order to wind the retrieve bag around the end of the push rod.

5. The device for retrieving tissue according to claim 1, wherein the closure device is sized to fit within the longitudinal slit when in a closed position.

6. The device for retrieving tissue according to claim 1, wherein the closure device comprises an open position and a closed position and the closure device is biased toward the open position.

7. The device for retrieving tissue according to claim 1, wherein a wring out device is assigned to the retrieve bag.

8. The device for retrieving tissue according to claim 1, wherein the retrieve bag further comprises at least one section that is not water permeable.

9. The device for retrieving tissue according to claim 8, wherein the at least one non-water permeable section is formed by a plastic foil.

10. The device for retrieving tissue according to claim 1, wherein the hydrophilic water permeable filter diaphragm comprises at least two layers that are identical.

11. The device for retrieving tissue according to claim 1, wherein the hydrophilic water permeable filter diaphragm comprises at least two layers that are different.

12. The device for retrieving tissue according to claim 1, wherein the one or more layers of filter materials is selected from: polyethersulfone, acrylic polymer, polyamide or polyethylene terephthalate, polysulfone, hydrophilized polytetrafluorethylene, cellulose acetate, cellulose nitrate, cellulose acetate with cellulose nitrate, nylon, polycarbonate and polyvinylidene difluoride.

13. The device for retrieving tissue according to claim 1, wherein the one or more layers of filter materials has a pore size of less than 3 μm.

14. The device for retrieving tissue according to claim 1, wherein the one or more layers of filter materials has a pore size of less than 2 μm.

15. The device for retrieving tissue according to claim 1, wherein the one or more layers of filter materials has a pore size of less than 0.2 μm.

* * * * *